(12) United States Patent
Carballada et al.

(10) Patent No.: US 7,981,167 B2
(45) Date of Patent: Jul. 19, 2011

(54) METHOD AND COMPOSITION FOR MAINTAINING HAIR DYE COLOR

(75) Inventors: Jose Antonio Carballada, Cincinnati, OH (US); Timothy Roy Nijakowski, Mason, OH (US); Bryan Patrick Murphy, Loveland, OH (US); Alexis M. J. A. Huyghues-Despointes, Villa Angla (VE); Axel Kalbfleisch, Darmstadt (DE)

(73) Assignee: The Procter & Gamble Company, Cincinnati, OH (US)

( * ) Notice: Subject to any disclaimer, the term of this patent is extended or adjusted under 35 U.S.C. 154(b) by 83 days.

(21) Appl. No.: 12/507,214

(22) Filed: Jul. 22, 2009

(65) Prior Publication Data

US 2010/0028279 A1    Feb. 4, 2010

Related U.S. Application Data

(60) Provisional application No. 61/085,222, filed on Jul. 31, 2008.

(51) Int. Cl.
*A61Q 5/10* (2006.01)

(52) U.S. Cl. ......... 8/405; 8/435; 8/552; 8/558; 132/202; 132/208

(58) Field of Classification Search ............... 8/405, 435, 8/552, 558; 132/202, 208
See application file for complete search history.

(56) References Cited

U.S. PATENT DOCUMENTS

| | | | |
|---|---|---|---|
| 3,472,243 A | 10/1969 | Wall |
| 3,472,604 A | 10/1969 | Dasher |
| 3,475,114 A | 10/1969 | Bolinger |
| 3,537,809 A | 11/1970 | Cednas |
| 3,583,408 A | 6/1971 | Wall |
| 3,619,114 A | 11/1971 | Anzuino |
| 3,619,117 A | 11/1971 | Anzuino |
| 3,619,118 A | 11/1971 | Anzuino |
| 3,633,591 A | 1/1972 | Anzuino |
| 3,634,022 A | 1/1972 | Robbins |
| 3,661,161 A | 5/1972 | Kalopissis |
| 3,676,550 A | 7/1972 | Anzuino |
| 3,678,157 A | 7/1972 | Kalopissis |
| 3,820,550 A | 6/1974 | Kinney |
| 3,882,114 A | 5/1975 | Kalopissis |
| 3,909,195 A | 9/1975 | Machell |
| 4,278,659 A | 7/1981 | Breuer |
| 4,338,295 A | 7/1982 | Highley |
| 4,588,760 A | 5/1986 | Jachowicz |
| 5,362,486 A | 11/1994 | Nandagiri |
| 6,740,317 B1 | 5/2004 | Cho |
| 2003/0175229 A1 | 9/2003 | Giroud |
| 2003/0235554 A1 | 12/2003 | Chahal |
| 2004/0016062 A1 | 1/2004 | Plos |
| 2004/0018162 A1 | 1/2004 | Bimczok |
| 2004/0156800 A1 | 8/2004 | Brun |

(Continued)

FOREIGN PATENT DOCUMENTS

DE    10259199 A1    6/2004

(Continued)

*Primary Examiner* — Eisa B Elhilo
(74) *Attorney, Agent, or Firm* — Angela K. Haughey

(57) ABSTRACT

A method of preventing color loss from dyed hair comprising the application of a hair care composition comprising from about 0.1% to about 20% of a sulfoalkyl(meth)acrylate compound, an alkylacetamido(meth)acrylate, or a mixture thereof, and a dermatologically acceptable carrier wherein the sulfoalkyl(meth)acrylate compound and the alkylacetamido(meth)acrylate undergo polymerization inside the hair fibers.

22 Claims, 1 Drawing Sheet

U.S. PATENT DOCUMENTS

| | | |
|---|---|---|
| 2004/0166071 A1 | 8/2004 | Pfaffernoschke |
| 2004/0261198 A1 | 12/2004 | Kainz |
| 2005/0129652 A1 | 6/2005 | Keller |
| 2007/0066506 A1 | 3/2007 | Behler |
| 2007/0275020 A1 | 11/2007 | Lendlein |
| 2008/0025936 A1 | 1/2008 | Keller |
| 2008/0066773 A1* | 3/2008 | Anderson et al. ............. 132/209 |
| 2008/0311050 A1 | 12/2008 | Lendlein |

FOREIGN PATENT DOCUMENTS

| | | |
|---|---|---|
| JP | 4208214 A2 | 7/1992 |
| JP | 10279436 A2 | 10/1998 |
| JP | 2000302648 A2 | 10/2000 |
| WO | WO0045777 A1 | 1/2000 |
| WO | WO0213773 A2 | 2/2002 |
| WO | WO0245665 A1 | 6/2002 |
| WO | WO2004062633 A1 | 7/2004 |

* cited by examiner

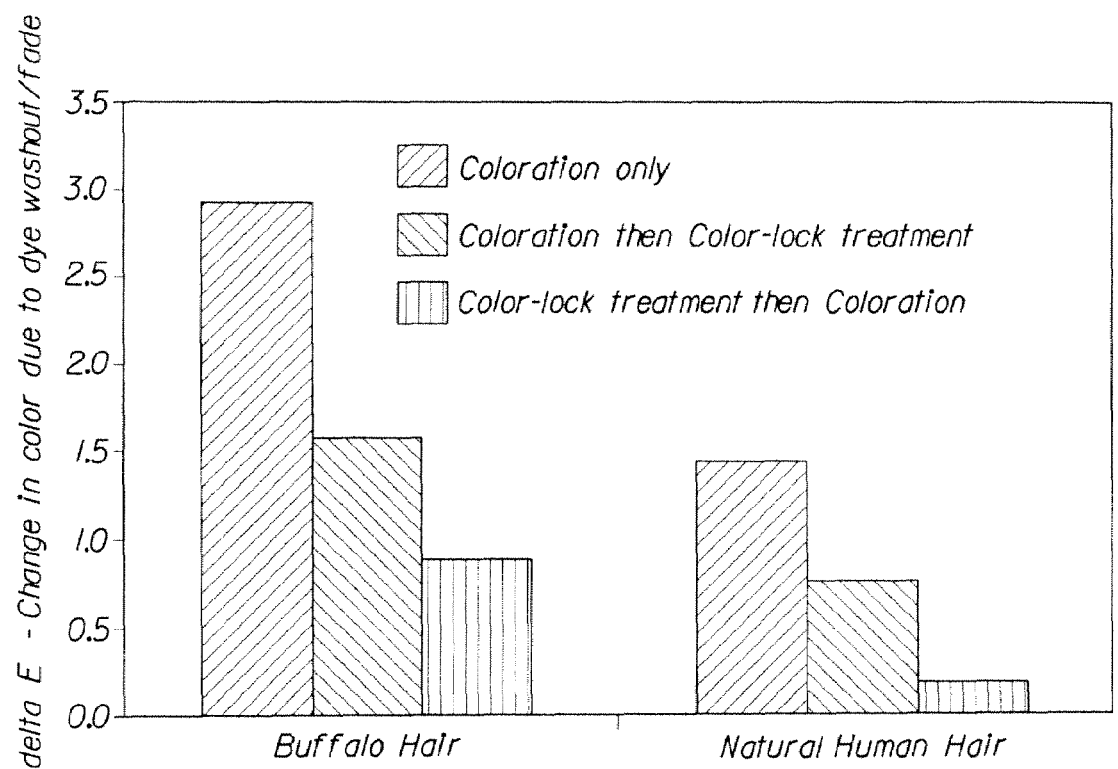

METHOD AND COMPOSITION FOR MAINTAINING HAIR DYE COLOR

CROSS REFERENCE TO RELATED APPLICATION

This Application claims the benefit of U.S. Provisional Application No. 61/085,222, filed on Jul. 31, 2008.

FIELD OF THE INVENTION

The present invention relates to a method and composition for preventing hair dye color loss via a method for application of a hair care composition comprising an ethylenic monomer.

BACKGROUND OF THE INVENTION

Hair dyes are formulated to give hair long-lasting and richly hued colors, but several factors from mechanical to environmental can accelerate color changes and fading.

The cuticle is the primary protection for the hair cortex. The cuticle is made up of cuticle cells which surround the cortex, or center of the hair. When the hair color is applied to the hair, the color molecules deposit throughout the cortex and cuticle regions of the fiber. The color molecules, however, do not remain permanently affixed inside the hair, rather as time passes, the color molecules diffuse out towards the surface of the fiber. As the color molecules diffuse towards the surface of the fiber, they come into more direct contact with water during washing. Therefore, the primary cause of color fading is due to the color diffusion and hair's contact with water. Washing both increases the rate of diffusion of the color molecules, as well as eventually washing the color molecules from the hair.

Based on the foregoing, there is a need for a method and composition for preventing color loss in dyed hair through the application of a composition which provides enhanced efficacy and performance for preventing color loss from hair fibers.

SUMMARY OF THE INVENTION

A method for preventing color loss from dyed hair comprising the steps of dyeing hair and applying to hair a composition comprising from about 0.1% to about 20% of at least one ethylenic monomer selected from the group consisting of sulfopropylacrylate, methyl 2-acetamidoacrylate and mixtures thereof, and a dermatologically acceptable carrier. A method for preventing color loss from dyed hair comprising the steps of applying to hair a composition comprising from about 0.1% to about 20% of an ethylenic monomer selected from the group consisting of sulfopropylacrylate compound, Methyl 2-acetamidoacrylate and mixtures thereof, wherein the ethylenic monomer has a molecular weight of less than 500 grams/mole; and a dermatologically acceptable carrier; and then dyeing the hair.

A method for preventing color loss from dyed hair comprising the steps of simultaneously applying to the hair a composition comprising from about 0.1% to about 20% of an ethylenic monomer selected from the group consisting of sulfopropylacrylate compound, Methyl 2-acetamidoacrylate and mixtures thereof, a dermatologically acceptable carrier; and a hair dye.

A hair care composition comprising: from about 0.1% to about 20% of at least one ethylenic monomer selected from the group consisting of sulfopropylacrylate, methyl 2-acetamidoacrylate and mixtures thereof, and a dermatologically acceptable carrier; and from about 0.1% to about 20% of a crosslinker selected from the group consisting of 1,4-bisacryloylpiperazine, methylenebisacrylamide, ethylenebisacrylamide, divinylbenzene, poly-ethyleneglycol di(meth)acrylate, ethylene glycol di(meth)acrylate, 1,3-butanediol di(meth)acrylate, 1,4-butanediol di(meth)acrylate, neopentyl glycol di(meth)acrylate, Bis[2-(methacryloyloxy)ethyl]phosphate, N,N'-bis(acryloyl)cystamine, N,N-Diallylacryalmide, triallyl cyanurate, 3-(Acryloyloxy)-2-hydroxypropyl methacrylate and mixtures thereof.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

FIG. 1 is a graph showing the delta E, or change in color due to dye wash out.

DETAILED DESCRIPTION OF THE INVENTION

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

"Hair," as used herein, means hair on the human head and scalp. "Hair shaft" means an individual hair, and may be used interchangeably with the term "hair."

"Internal region of the hair shaft," as used herein, means any non-surface portion of the hair shaft, including the inner portion of the cuticle. "Non-surface portion" may be understood to mean that portion of the hair that is not in direct contact with the outside environment.

"Proximal to the scalp," as used herein, means that portion of an extended, or substantially straightened, hair shaft that is closer in distance to the scalp than to the end of the hair. Thus, about 50% of the hair would be considered proximal to the scalp, and about 50% of the hair would be distal to the scalp. "x cm proximal to the scalp" means a distance "x" along the hair, with one endpoint being on or directly adjacent to the scalp, and the second endpoint being measured "x" centimeters along the length of the extended or substantially straightened hair.

"Dermatologically-acceptable carrier," as used herein, means that the compositions or components described are suitable for use in contact with human keratinous tissue without undue toxicity, incompatibility, instability, allergic response, and the like.

"Derivatives," as used herein, includes but is not limited to, amide, ether, ester, amino, carboxyl, acetyl, and/or alcohol derivatives of a given compound.

"Monomer," as used herein, means a discrete, non-polymerized chemical moiety capable of undergoing polymerization in the presence of an initiator.

"Ethylenic monomer," as used herein, means a chemical species that contains an olefenic carbon-carbon double bond (C=C) and is capable of undergoing polymerization in the presence of an initiator.

"Chemically modify," or grammatical equivalents thereof, as used herein, means that a chemical moiety such as monomer and/or crosslinker and/or polymer, stably affixes to a second chemical moiety, for example, a keratin protein, another component of hair, and/or another monomer or crosslinker.

"Stably affix" is understood to include both covalent and non-covalent forms of chemical bonds that once formed, remain unchanged through wetting, washing, styling and other types of hair treatment. In general, stably affixed chemical moieties may not be removed from the hair without damaging or substantially destroying the hair.

"Color lock" as used herein, is determined by the Color Fastness to Washing of Dyed Hair with Shampoo Method. One example of determining color lock is as follows: First, two (2) hair samples in the form of a 2 g pony-tail swatch are colored with a commercial hair dye product such as 'Nice 'n Easy 120b Level 3 permanent' per instructions. The resulting color of the swatches is measured using a Hunter Colorimeter with D65 illumination at a 2 degree observance angle to determine Lab color space values for each swatch. One of the colored swatches is treated with the color-lock treatment. Subsequently, both swatches are shampoo washed for 15 seconds and rinsed for 30 seconds and dried. This wash process is repeated five (5) additional times. The shampoo used for washing is Lifetex color repair shampoo. The ending color of the switches is again measured using the same Hunter Colorimeter as before. The change in color resulting from dye loss is calculated from the difference in Lab values from immediately after coloring and after all the washes and reported as the value ΔE. A smaller ΔE represents less dye loss. The color lock is improved if the ΔE of the colored hair with the treatment described in the present invention after washing is less than the ΔE of the same hair lot with the same color after washing.

$$\Delta L = L_{before\ washes} - L_{after\ washes}$$

$$\Delta a = a_{before\ washes} - a_{after\ washes}$$

$$\Delta b = b_{before\ washes} - b_{after\ washes}$$

$$\Delta E = [(\Delta L)^2 + (\Delta a)^2 + (\Delta b)^2]^{1/2}$$

"Dye Diffusion" as used herein, is determined by the Dye Removal from Hair Diffusion Test Method. One example of determining dye diffusion is as follows: First, two (2) hair samples in the form of a 2 g pony-tail swatch are colored with a professional hair dye product such as Koleston Perfect Level 3 permanent' by the normal process and dried. One of the colored swatches is treated with the color-lock treatment. Subsequently both hair swatches are submersed in separate 300 ml beakers of demineralized water with stirring at 100 rpm with a magnetic stir bar at 25° C. for 3 hours. Finally, an aliquot of solution from each beaker is transferred into a 10 mm spectrophotometer cell and the absorbance is measured at the appropriate wavelength for the coloring agent of interest in a Shimadzu UV-1601 UV-Visible Spectrophotometer. The concentration of the dye is determined by measurement of the absorbance of the solution against the solvent by use of the Lambert-\beer law which states the relationship between the concentration, sample thickness, and absorbance. Higher dye concentration in the solution means greater diffusion of dye from the hair to the solution. Dye diffusion is minimized if the concentration of dye in the solution containing the colored hair with the treatment described in the present invention is less than the concentration of dye in the solution containing hair of the same lot and color.

$$A = \epsilon b c$$

A=absorbance
$\epsilon$=molar absorptivity
b=path length through the sample
c=concentration of the chromophoric species (dye).

"Reserve alkalinity," as used herein, means the relative strength and apparent concentration of the base used to adjust the pH, measured as described in ASTM D 1121, wherein the base of the present invention is substituted for the antifreeze used in the method.

"Reducing Composition" as used herein, means any form of product containing a reducing agent such as thioglycolate (about 0.1%-about 5% by weight) that is used to pre-treat the hair to induce greater swelling and uptake of actives.

"Finishing Composition" as used herein, means a neutralizing and/or oxidizing composition and can be any form of product containing an oxidizer such as hydrogen peroxide (about 0.1%-about 3% by weight) and buffered at low pH that is used to neutralize reduction and alkaline effects in the hair.

"Kit," as used herein, means a packaging unit comprising a color lock composition and a separately packaged second composition, as described herein.

"Separately packaged," as used herein, means any form of packaging that prevents a color lock composition from coming into physical contact, or admixing, with a second composition. "Separately packaged" may mean that the individual compositions are packaged in separate containers, or alternatively in a single container partitioned such that the compositions are not in physical contact.

"Implement," as used herein, means a device used to facilitate application of a composition to the hair and/or manipulation of the hair. Examples of implements include, but are not limited to, a comb, a means for directed delivery (e.g., an applicator or tube), a covering for the hair (e.g., plastic bag, shower cap, etc.), and combinations thereof.

"Energy delivery device," as used herein, means any device used to deliver energy to keratinous tissue, including the hair and scalp. "Delivery of energy," means that the surface of the keratinous tissue is exposed to the energy emanating from the energy delivery device, where it may penetrate to the desired layers of the tissue, including the hair shaft and/or hair follicle. Energy includes but is not limited to energy in the form of light, heat, sound (including ultrasonic waves), electrical energy, magnetic energy, electromagnetic energy (including radiofrequency waves and microwaves), and combinations thereof.

I. Method for Preventing Color Loss from Dyed Hair

The compositions described herein are particularly useful in preventing color loss from hair which has been previously treated with either an oxidative ("level 3") or preformed ("level 2") hair dye. "Dyed" or "previously dyed" hair includes hair which contains hair dye molecules resulting from a hair dyeing process or otherwise visually exhibits a hair color which is the result of a hair dye treatment.

The present invention relates to a method for preventing color loss from dyed hair comprising the steps of dyeing hair (or beginning with previously dyed hair); and applying to the hair a composition. The invention also relates to the use of this composition for preventing color loss from dyed hair. The method of preventing color loss herein comprises the steps of contacting or treating the hair, which has previously been dyed, is currently being dyed, or is going to be dyed in the future with a composition comprising from about 0.1% to about 20% of an ethylenic monomer, and, a dermatologically acceptable carrier (hereinafter "color lock composition"). The hair dye can be applied before, during, or after treating the hair with the color lock composition. Additionally, if the hair was previously dyed, or dyed during the application of the color lock composition, a dye can be applied to the hair immediately following the color lock composition in order to freshen the hair color.

It is believed that these color lock compositions form a polymer inside the hair fiber which slows the loss of the color molecule(s) resulting from: i) filling up the channels in the hair cuticle, thus blocking the path for diffusion of the color molecules to the hair surface, and ii) by stably affixing to the color molecule(s) thus slowing the rate of diffusion or the color molecules to the fiber surface The color lock compositions mentioned herein may stably affix to the cuticle cells. The color molecules may have an affinity for the polymer formed from these color lock compositions, thus the color molecules may be retained to the internal regions of the hair shaft as long as the formed polymer is present within the hair fiber.

As shown in FIG. 1, the delta E, or change in color due to dye wash out, is smaller for the samples which have been treated with the color lock compositions. Thus, the hair dye is retained to the internal regions of the hair shaft after washing if the hair is treated with the color lock composition.

II. Color Lock Compositions

The present invention comprises a color lock composition comprising an ethylenic monomer. The ethylenic monomer is of a size suitable to penetrate the hair shaft and is soluble or dispersible in the carrier. The color lock composition may have a pH of about 7.0 and below, alternatively of from about 3.0 to about 7.0, and alternatively of from about 5.0 to about 6.0. In all embodiments, "about," when used in reference to pH, is understood to mean±0.5 pH unit.

In one embodiment the ethylenic monomer is a sulfoalkyl (meth)acrylate compound. "Sulfoalkyl(meth)acrylate compound," as used herein, is understood to include derivatives, salts and/or isomers of sulfoalkyl(meth)acrylate. The sulfoalkyl(meth)acrylate compounds of the present invention are understood to be in a non-polymerized form, and do not include polymers of sulfoalkyl(meth)acrylate. One example of a useful sulfoalkyl(meth)acrylate compound is 3-sulfopropylacrylate, CAS #31098-20-1. Sulfopropylacrylate compounds also may be known as sulfopropyl acrylate esters; sulfoalkylpropenoate; acrylic acid propyl ester sulfonates; propenoic acid sulfoalkyl ester; and/or sulfoalkylpropenoic acid ester. The color lock composition may comprise from about 0.1% to about 20%, alternatively from about 1% to about 15%, alternatively from about 5% to about 10%, alternatively from about 0.1% to about 10%, and alternatively from about 10% to about 20% of a sulfopropylacrylate compound.

In another embodiment the ethylenic monomer is an alkylacetamidoacrylate compound. "Alkylacetamidoacrylate" as used herein, is understood to include derivatives, salts and/or isomers of alkylacetamidoacrylate. The alkylacetamidoacrylate compounds of the present invention are understood to be in a non-polymerized form, and do not include polymers of alkylacetamidoacrylate. One example of a useful alkylacetamidoacrylate compound is Methyl-2-acetamidoacrylate, CAS #35356-70-8. The color lock composition may comprise from about 0.1% to about 20%, alternatively from about 1% to about 15%, alternatively from about 5% to about 10%, alternatively from about 0.1% to about 10%, and alternatively from about 10% to about 20% of a methyl 2-acetamidoacrylate compound.

The color lock composition may also comprise at least one ethylenic monomer having a size suitable to penetrate the hair shaft and a molecular weight of 500 g/mole or less, alternatively from about 50 g/mole to about 500 g/mole, alternatively from about 75 g/mole to about 400 g/mole, and alternatively from about 100 g/mole to about 400 g/mole. Examples of ethylenic monomers suitable for use in the color lock composition of the present invention include, but are not limited to, mesaconic acid, 2-pentenoic acid, tiglic acid, tiglic acid esters, furan-3-acrylic acid, 2-acrylamido-2-methyl-1-propanesulfonic acid, maleamic acid, 3-aminocrotonic acid, crotonic acid esters, itaconic anhydride, trimethylsilylacrylate, poly(ethyleneglycol)acrylates, N-vinylacetamide, 2-acetamidoacrylic acid, vinylsulfonic acid, tetrahydrofurfurylacrylate, N-methyl-N-vinylacetamide, vinylpropionate, vinylanisole, vinylcrotonate, methyl 3-hydroxy-2-methylenebutyrate, methacryloyl-L-lysine, N-(2-hydroxypropyl) methacrylamide, 2-acrylamidodiglycolic acid, 2-ethoxyethyl acrylate, 2-butoxyethyl acrylate, N-isopropylmethacryalmide, 2-aminoethyl methacrylate, 2-bromoethyl acrylate, 3-(dimethylamino)propyl acrylate, (3-acrylamidopropyl)trimethyl ammonium salt, [2-(acryloyloxy)ethyl]-trimethylammonium salt, alkylacetamidoacrylate, sulfoalkyl(meth)acrylate and salts, isomers, derivatives and mixtures thereof. The color lock composition may comprise from about 0.1% to about 20%, alternatively from about 1% to about 15%, alternatively from about 5% to about 10%, alternatively from about 0.1% to about 10%, and alternatively from about 10% to about 20%, of an ethylenic monomer.

One method of selecting compounds for this technology is selecting from a group of ethylenic monomers, the monomer can be from the family of acrylates, acrylamides, or vinyls. The monomer can be water soluble and less than 500 amu's in molecular weight. The monomer can penetrate hair to the extent of 5-10% by weight using an aqueous carrier and gravimetric techniques to measure. The monomer may react to about 75% completion within 30 minutes at 35° C. in presence of initiator. In another embodiment the monomer may react from about 90% to about 100% completion within 30 minutes at 35° C. in presence of initiator. The final resulting polymer can be water soluble or remove-able from the surface of hair via normal shampooing. These monomers can be used alone or as co-monomers with other actives to enhance reactivity and solubility.

In one embodiment, the ratio of the weight percentage of the sulfopropylacrylate compound, the methyl 2-acetamidoacrylate, and/or a mixture thereof to the weight percentage of the monomer is from about 1:12 to about 12:1, alternatively from about 1:10 to about 10:1, alternatively from about 1:5 to about 5:1, alternatively from about 12:1 to about 1:1, alternatively from about 10:1 to about 1:1 and alternatively from about 5:1 to about 1:1.

The color lock composition further may comprise at least one crosslinker having a molecular weight of a size suitable to penetrate the hair shaft and a molecular weight of 500 g/mole or less, alternatively from about 100 g/mole to about 500 g/mole, alternatively from about 100 g/mole to about 400 g/mole, and alternatively from about 200 g/mol to about 400 g/mole. Examples of crosslinkers suitable for use in the color lock composition of the present invention include, but are not limited to, 1,4-bisacryloylpiperazine, methylenebisacrylamide, ethylenebisacrylamide, divinylbenzene, poly-ethyleneglycol di(meth)acrylate, ethylene glycol di(meth)acrylate, 1,3-butanediol di(meth)acrylate, 1,4-butanediol di(meth)acrylate, neopentyl glycol di(meth)acrylate, Bis[2-(methacryloyloxy)ethyl]phosphate, N,N'-bis(acryloyl)cystamine, N,N-Diallylacryalmide, triallyl cyanurate, 3-(Acryloyloxy)-2-hydroxypropyl methacrylate and mixtures thereof.

In one embodiment, the ratio of the weight percentage of the sulfopropylacrylate compound, the methyl 2-acetamidoacrylate, and/or the mixture thereof to the weight percentage of the crosslinker is from about 50:1 to about 10:1, alternatively from about 40:1 to about 10:1, and alternatively from about 20:1 to about 10:1.

The color lock composition further may comprise from about 0.01% to about 1% of at least one organic or inorganic catalyst. Non-limiting examples of suitable organic catalysts include 2-pyrrolidinoethanol, 1-piperidine-ethanol, 4-methylmorpholine, 2-morpholinoethanol, tetramethylethylenediamine, and mixtures thereof. Non-limiting examples of suitable inorganic catalysts include salts and/or hydrates of cerium, cobalt, manganese, iron, nickel, copper, and mixtures thereof.

The present invention further may comprise, in some embodiments, a second composition comprising an initiator, useful for promoting binding of an ethylenic monomer and/or crosslinker to the keratin and/or to another monomer. The second composition may comprise from about 0.001% to about 5%, alternatively from about 0.01% to about 3%, and alternatively from about 0.1% to about 1%, of an initiator. Examples of suitable classes of initiators include, but are not limited to, peroxidisulfates, peroxides, peracids, percarbonate, phosphates, manganates, borates, bis-alkyamidines, sulfites, peroxyesters, bis-cyanocarboxylic acids, alpha-amino acetic acids, and mixtures thereof. Non-limiting examples of suitable initiators include sodium peroxydisulfate, 2,2'-azobis(2-methylpropionamidine)dihydrochloride, 2,2'-azobisisobutyronitrile, benzoyl peroxide, peracetic acid, ammonium cerium(IV) nitrate, hydroxymethanesulfinic acid and mixtures thereof. The second composition further may have a pH of above 7.0, alternatively of from about 7.0 to about 12.0, alternatively of from about 8.0 to about 12.0, and alternatively of from about 9.0 to about 11. In an alternative embodiment, the second composition has a pH of about 7.0 and below.

The present invention may comprise a third composition comprising a base, which is packaged separately from the first and the second composition, and which is useful for adjusting the pH of one, or a combination of any, of the compositions disclosed herein. The third, or pH adjusting, composition may have a pH of above 7.0, alternatively of from about 7.0 to about 12.0, alternatively of from about 8.0 to about 12.0, and alternatively of from about 9.0 to about 11.0. Additionally or alternatively, the third composition has a reserve alkalinity from about 1 to about 40, and alternatively from about 10 to about 30. Non-limiting examples of classes of suitable bases include, but are not limited to ammonium salts, amines, hydroxides, metasilicates, and mixtures thereof. Non-limiting examples of suitable bases include sodium hydroxide, potassium hydroxide, sodium metasilicate, ammonium hydroxide, ethanolamine, aminomethylpropanol, ammonium carbonate, and mixtures thereof.

The third composition further may comprise from about 0.1% to about 10%, and alternatively from about 0.5% to about 5%, of at least one organic or inorganic salt. Examples of organic salts include, but are not limited to, salts formed by reacting at least one anion chosen from phosphates, borates, silicates, bicarbonates, carbonates, chlorates, nitrates, halides (including, but not limited to, chlorides), and/or sulfonates, with at least one cation chosen from potassium, sodium, strontium, cadmium, calcium, ammonium (such as tetraalkylammonium and arylammonium), phosphonium, barium, lithium, and/or magnesium. Non-limiting examples of suitable organic salts include sodium monobutyl and dibutyl phosphates and sodium monoethyl and diethyl phosphates. In one embodiment, the salt comprises an inorganic cation. In one embodiment, the inorganic cation is a multivalent cation selected from the group consisting of magnesium, calcium, strontium, barium, copper, zinc, iron, nickel, cobalt, manganese, aluminum, silver, lanthanum, and complexes and mixtures thereof.

Dermatologically Acceptable Carrier

The compositions of the present invention may comprise from about 60% to about 99.9%, alternatively from about 70% to about 95%, and alternatively from about 80% to about 90%, of a dermatologically acceptable carrier. Carriers suitable for use with the composition(s) of the present invention include, for example, those used in the formulation of hair sprays, mousses, tonics, gels, and leave-on conditioners. The carrier may comprise water; organic oils; silicones such as volatile silicones, amino or non-amino silicone gums or oils, and mixtures thereof, mineral oils; plant oils such as olive oil, castor oil, rapeseed oil, coconut oil, wheatgerm oil, sweet almond oil, avocado oil, macadamia oil, apricot oil, safflower oil, candlenut oil, false flax oil, tamanu oil, lemon oil and mixtures thereof, waxes; and organic compounds such as $C_2$-$C_{10}$ alkanes, acetone, methyl ethyl ketone, volatile organic $C_1$-$C_{12}$ alcohols, esters of $C_1$-$C_{20}$ acids and of $C_1$-$C_8$ alcohols such as methyl acetate, butyl acetate, ethyl acetate, and isopropyl myristate, dimethoxyethane, diethoxyethane, $C_{10}$-$C_{30}$ fatty alcohols such as lauryl alcohol, cetyl alcohol, stearyl alcohol, and behenyl alcohol; $C_{10}$-$C_{30}$ fatty acids such as lauric acid and stearic acid; $C_{10}$-$C_{30}$ fatty amides such as lauric diethanolamide; $C_{10}$-$C_{30}$ fatty alkyl esters such as $C_{10}$-$C_{30}$ fatty alkyl benzoates; hydroxypropylcellulose, and mixtures thereof. In one embodiment, the carrier comprises water, fatty alcohols, volatile organic alcohols, and mixtures thereof.

Finishing Composition

The composition(s) of the present invention may further comprise a finishing composition including, but not limited, any form of product comprising an oxidizer such as hydrogen peroxide (about 0.1%-about 3% by weight) and buffered at low pH that is used to neutralize reduction and alkaline effects in the hair.

Optional Components

The composition(s) of the present invention may further comprise one or more optional components known or otherwise effective for use in hair care or personal care products, provided that the optional components are physically and chemically compatible with the essential components described herein, or do not otherwise unduly impair product stability, aesthetics, or performance. Non-limiting examples of such optional components are disclosed in International Cosmetic Ingredient Dictionary, Ninth Edition, 2002, and CTFA Cosmetic Ingredient Handbook, Tenth Edition, 2004, both of which are incorporated by reference herein in their entirety. Some non-limiting examples of such optional components are disclosed below, and include plasticizers, surfactants (which may be anionic, cationic, amphoteric or non-ionic), neutralizing agents, propellants, hair conditioning agents (e.g., silicone fluids, fatty esters, fatty alcohols, long chain hydrocarbons, cationic surfactants, etc.), emollients, lubricants and penetrants such as various lanolin compounds, vitamins, proteins, preservatives, dyes, tints, bleaches, reducing agents and other colorants, sunscreens, thickening agents (e.g., polymeric thickeners, such as xanthan gum), physiologically active compounds for treating the hair or skin (e.g., anti-dandruff actives, hair growth actives), non-polymeric thickeners including clays, and perfume.

The composition(s) of the present invention further may comprise from about 0.1% to about 10%, and alternatively from about 0.2% to about 5.0%, of a gelling agent to help provide the desired viscosity to the composition(s). Non-limiting examples of suitable optional gelling agents include crosslinked carboxylic acid polymers; unneutralized crosslinked carboxylic acid polymers; unneutralized modified crosslinked carboxylic acid polymers; crosslinked ethylene/maleic anhydride copolymers; unneutralized crosslinked ethylene/maleic anhydride copolymers (e.g., EMA 81 commercially available from Monsanto); unneutralized crosslinked allyl ether/acrylate copolymers (e.g., Salcare™ SC90 commercially available from Allied Colloids); unneutralized crosslinked copolymers of sodium polyacrylate, mineral oil, and PEG-1 trideceth-6 (e.g., Salcare™ SC91 commercially available from Allied Colloids); unneutralized crosslinked copolymers of methyl vinyl ether and maleic anhydride (e.g., Stabileze™ QM-PVM/MA copolymer commercially available from International Specialty Products); hydrophobically modified nonionic cellulose polymers; hydrophobically modified ethoxylate urethane polymers (e.g., Ucare™ Polyphobe Series of alkali swellable polymers commercially available from Union Carbide); and combinations thereof. In this context, the term "unneutralized" means that the optional polymer and copolymer gelling agent materials contain unneutralized acid monomers. Preferred gelling agents include water-soluble unneutralized crosslinked ethylene/maleic anhydride copolymers, water-soluble unneutralized crosslinked carboxylic acid polymers, water-soluble hydrophobically modified nonionic cellulose polymers and surfactant/fatty alcohol gel networks such as those suitable for use in hair conditioning products.

III. Methods of Use

The present invention further describes methods of using the composition(s) of the present invention to chemically modify the internal portion of a hair shaft. The method comprises the step of applying to hair a color lock composition and an initiator as described herein. The initiator may form part of a second composition. The composition(s) may be applied by a variety of means, including with the fingers, hands, with an implement and/or with an energy delivery device. The composition(s) may be applied to wet hair or to dry hair. The amount applied will vary, and will depend upon the thickness and length of the hair, and the desired effect. In one embodiment, the composition(s) may be applied to substantially all of the hair, and alternatively to a portion of the hair. In one embodiment, the composition(s) may be applied to a portion of the hair that is proximal to the scalp, for example, from about 0 cm to about 10 cm, and alternatively from about 0 cm to about 5 cm proximal to the scalp. This may be desirable, for example, to "touch up" the roots of newly grown hair between treatments.

In one embodiment, the color lock composition comprising the monomer, and the second composition comprising the initiator are mixed prior to application to the hair, and applied to the hair as a single composition. For example, the first and second compositions may be mixed together one minute or less prior to application to the hair. Optionally, heat may be applied to the hair after applying the mixture. Alternatively, the color lock composition comprising the monomer is applied to the hair prior to application of the second composition comprising the initiator, without prior mixing. Alternatively, the second composition comprising the initiator is applied to the hair prior to application of the color lock composition comprising the monomer. The time interval between application of the color lock and the second composition may vary, and may comprise from about 5 minutes to about 60 minutes, alternatively from about 15 minutes to about 45 minutes, and alternatively may be about 30 minutes. Optionally, heat may be applied to the hair for all or for a portion of the time period between application of the compositions.

A suitable initiator also may include light energy. Therefore, in one embodiment, the color lock composition may be applied to the hair, and the hair exposed to light energy. One non-limiting example includes allowing the composition to remain on the hair under a light source for about 5 minutes to about 30 minutes.

The method further may comprise the step of applying a third, or pH adjusting composition to the hair. The third composition may be mixed with the first and/or second composition, such that the final pH of the mixture of compositions is greater than 7.0, alternatively from 7.0 to about 12.0, alternatively from about 8.0 to about 12.0, and alternatively is from about 9.0 to about 11.0.

The method further may comprise the step of applying a fourth, or reducing, composition to the hair. In one embodiment, the reducing composition is applied prior to one or more compositions described herein and is allowed to remain on the hair from about 5 minutes to about 60 minutes, and in another embodiment the reducing composition remains on the hair for about 15 minutes, after which time the composition is substantially removed from the hair, for example by rinsing with water. Optionally, heat may be applied to the hair for all or for a portion of the time during which the composition remains on the hair.

The method further may comprise a finishing step of applying a finishing composition which can be a neutralizing, and/or oxidizing composition to the hair. In one embodiment, the finishing composition is applied after one or more of the compositions described herein are substantially removed from the hair, for example by rinsing with water and is allowed to remain on the hair from about 1 minute to about 5 minutes.

After treatment with one or more compositions of the present invention, the hair may exhibit one or more benefits in addition to color lock, including but not limited to increased shape retention and/or durability, increased appearance of volume, increased resistance to the effects of humidity, for example, upon the style of the hair and/or upon the condition of the hair. Examples include all day hold of style, excellent curl definition, increased body and/or fullness, the ability to curl straight hair, and/or the ability to straighten curly hair.

IV. Kit

The present invention further describes a kit comprising a color lock composition and optionally a second composition as described herein. The first and the second composition may be packaged in separate containers within the kit, and alternatively may be packaged in a single container which is capable of preventing admixing of the two compositions. The packaging may be of a size suitable for a single application, or unit dose, of the first and/or second composition. The kit may comprise a number of unit doses suitable for an indicated treatment regimen.

The kit further may comprise at least one additional composition selected from the group consisting of a pH adjustor, a reducing composition, and combinations thereof. In one embodiment, the pH adjustor has a reserve alkalinity as described herein and packaged in a container having a volume, such that when the contents of the container are mixed with the first and/or the second composition, the pH of the resulting mixture of compositions is greater than 7.0.

The kit further may comprise at least one additional component selected from the group consisting of a shampoo, a conditioner, a neutralizer, a colorant, a styling aid such as a gel, a mousse, a pomade, etc., an implement, an energy delivery device, instructions for complying with a treatment regimen, and combinations thereof. Examples of energy delivery devices include, but are not limited to light sources, including UV, visible light and infrared light, temperature change elements, hair dryers, heaters such as irons and heated curlers, ultrasonic devices, etc.

The kit further may comprise instructions for complying with a hair treatment regimen. The treatment regimen may comprise one or methods of use described herein, and may be directed toward treatment by a professional stylist or toward treatment by a consumer who is not a professionally-trained stylist.

V. Article of Commerce

The present invention further describes an article of commerce comprising a color lock composition and/or a second composition, as described herein, and a communication pertaining to the compositions. The communication may be printed material attached directly or indirectly to packaging, for example to a kit that contains the compositions. Alternatively, the communication may be placed directly or indirectly near at least one composition. Alternatively, the communication may be an electronic or a broadcast message that is associated with the applicator and/or the composition. The communication may comprise images comparing the appearance of a person prior to use of the compositions to the appearance of the same person after use of the composition. One example of a suitable communication would be one directing a consumer having faded hair dye to apply the composition(s) to the hair to increase the length of time hair remains the desired hair color. Another example of a suitable communication would be one directing a professional hair stylist to apply the composition to clients desiring a longer lasting hair color.

EXAMPLES

The following describes one non-limiting example of a method of using the compositions of the present invention to increase the length of time mammalian hair remains the desired color when dyed:

Begin with dry hair. If the hair is washed first, make sure hair is thoroughly dried, and comb the hair sufficiently to detangle. Mix together by stirring or vigorously shaking, for about 30 seconds, about 50 ml of a color lock composition (Composition I—described below), about 1.0 ml of a second composition (Composition II—described below), and about 49 ml of a pH adjusting composition (Composition III—described below). Apply a suitable amount, as described above in this example, of the mixture to the hair. Gently massage the mixture into the hair, avoiding contact of the composition with the skin and/or scalp and eyes. Allow the composition to remain on the hair, uncovered, for about 30 minutes at 35° C.±5° C. Gently wash the hair (preferably with clarifying shampoo) and rinse thoroughly with water. Optionally, a conditioner may be applied to the hair. The hair may further be dried and styled as desired. The application of the compositions may be preceded with a hair dying step, may be performed on hair dyed at an earlier date, may occur simultaneously with a hair dyeing step, or may be subsequently followed with a hair dyeing step. Additionally, if the hair is dyed prior to the application of the aforementioned compositions, the treatment may be followed with a subsequent application of hair dye to freshen the color.

| | Composition I | | | | |
|---|---|---|---|---|---|
| | Example 1 wt. % | Example 2 wt. % | Example 3 wt. % | Example 4 wt. % | Example 5 wt. % |
| Ingredients: | | | | | |
| 1 Purified Water | qs | qs | qs | qs | qs |
| 2 Hydroxypropylmethyl cellulose | 0.1 | 0.1 | 0.2 | 0.2 | 0.3 |
| 3 Polyquaterium-10 | 1.0 | — | 1.0 | — | 1.2 |
| 4 Cremophor EL | 0.2 | — | 0.2 | 0.2 | 0.2 |
| 5 Tetrasodium EDTA | 0.05 | 0.05 | 0.05 | 0.05 | 0.05 |
| 6 Phenoxyethanol | 0.25 | 0.25 | 0.25 | 0.25 | 0.25 |
| 7 Sodium Benzoate | 0.125 | 0.125 | 0.125 | 0.125 | 0.125 |
| 8 Ascrobic Acid | 0.05 | 0.05 | 0.05 | 0.05 | 0.05 |
| 9 1,2-Hexanediol | — | 2 | 2 | — | — |
| 10 Isopropyl alcohol | 10 | — | 10 | — | — |
| 11 Genepol C-100 | — | 0.2 | — | 0.2 | 0.2 |
| Monomer Actives: | | | | | |
| 12 Sulfopropylacrylate potassium salt | 0.1 | 12 | 4 | — | 8 |
| 13 Methyl 2-Acetamidoacrylate | 12 | — | 4 | 8 | — |
| 14 3-(Acryloyloxy)-2-hydroxypropyl methacrylate | — | 1.5 | 1 | — | 0.5 |
| Fragrance: | | | | | |
| 15 Nourrissant 124 | — | 0.25 | 0.25 | 0.25 | 0.25 |

Mix the ingredients as follows, with continuous stirring. Add water to a suitable mixing vessel. Heat to about 80° C. Add ingredients 2-11 and stir until dissolved and allow temperature to again reach about 80° C. Maintain temperature at about 80° C. for about 10 minutes. Cool to below 30° C. Add ingredients 12-15 and continue to stir until dissolved.

Composition II

| Ingredients: | Example 1 wt. % | Example 2 wt. % | Example 3 wt. % | Example 4 wt. % | Example 5 wt. % |
|---|---|---|---|---|---|
| 16 Sodium Persulfate | 100 | — | 90 | 10 | 50 |
| 17 Hydroxymethanesulfinic acid monosodium salt | — | 100 | — | 90 | 50 |
| 18 Copper (III) Nitrate | — | — | 10 | — | — |

Combine all ingredients.

Composition III

| Ingredients: | Example 1 wt. % | Example 2 wt. % | Example 3 wt. % | Example 4 wt. % | Example 5 wt. % |
|---|---|---|---|---|---|
| 19 Purified Water | qs | qs | qs | qs | qs |
| 20 Ammonium Hydroxide (5N standard) | 8 | — | — | 10 | 10 |
| 21 Sodium Hydroxide (1N standard) | — | 10 | — | — | — |
| 22 Sodium Metasilicate | — | — | 10 | — | — |
| 23 Strontium Chloride | — | 5 | 5 | — | — |

Add water to a suitable mixing vessel. Add ingredients 20-23 and continue to stir until dissolved.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

Whereas particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for preventing color loss from dyed hair comprising the steps of:
   a) dye hair;
   b) apply to hair a composition comprising:
      i. from about 0.1% to about 20% of at least one ethylenic monomer selected from the group consisting of sulfopropylacrylate, alkylacetamidoacrylate and mixtures thereof, and
      ii. a dermatologically acceptable carrier.

2. The method of claim 1, wherein the composition further comprises an initiator selected from the group consisting of peroxidisulfates, peroxides, peracids, percarbonate, phosphates, manganates, borates, bis-alkyamidines, sulfites, peroxyesters, bis-cyanocarboxylic acids, alpha-amino acetic acids, sodium peroxydisulfate, 2,2'-azobis(2-methylpropionamidine)dihydrochloride, 2,2'-azobisisobutyronitrile, benzoyl peroxide, peracetic acid, ammonium cerium(IV) nitrate, hydroxymethanesulfinic acid, and mixtures thereof.

3. The method of claim 1, wherein the composition is mixed prior to application to the hair.

4. The method of claim 1, further comprising the step of applying heat to the hair.

5. The method of claim 1, wherein the composition is applied to a portion of the hair proximal to the scalp.

6. The method of claim 1, wherein the composition further comprises from about 0.1% to about 20% of at least one additional compound selected from the group consisting of an ethylenic monomer, a crosslinker, and mixtures thereof, wherein the additional compound has a molecular weight of less than 500 g/mole.

7. The method of claim 6, wherein the composition comprises a crosslinker.

8. The method of claim 7, wherein the crosslinker is selected from the group consisting of 1,4-bisacryloylpiperazine, methylenebisacrylamide, ethylenebisacrylamide, divinylbenzene, poly-ethyleneglycol di(meth)acrylate, ethylene glycol di(meth)acrylate, 1,3-butanediol di(meth)acrylate, 1,4-butanediol di(meth)acrylate, neopentyl glycol di(meth)acrylate, Bis[2-(methacryloyloxy)ethyl]phosphate, N,N'-bis(acryloyl)cystamine, N,N-Diallylacryalmide, triallyl cyanurate, 3-(Acryloyloxy)-2-hydroxypropyl methacrylate and mixtures thereof.

9. The method of claim 1, wherein the composition further comprises from about 0.1% to about 1% of a catalyst.

10. The method of claim 1, further comprising a second application of hair dye.

11. The method of claim 1, further comprising the step of adding a composition to the hair selected from the group consisting of a neutralizing composition, an oxidizing composition and a combination thereof.

12. A method for preventing color loss from dyed hair comprising the steps of:

a) apply to hair a composition comprising:

i. from about 0.1% to about 20% of an ethylenic monomer selected from the group consisting of sulfopropylacrylate compound, alkylacetamidoacrylate and mixtures thereof, wherein the ethylenic monomer has a molecular weight of less than 500 grams/mole; and ii. a dermatologically acceptable carrier; and b) dye hair.

13. The method of claim 12, wherein the composition comprises an initiator selected from the group consisting of peroxidisulfates, peroxides, peracids, percarbonate, phosphates, manganates, borates, bis-alkyamidines, sulfites, peroxyesters, bis-cyanocarboxylic acids, alpha-amino acetic acids, sodium peroxydisulfate, 2,2'-azobis(2-methylpropionamidine)dihydrochloride, 2,2'-azobisisobutyronitrile, benzoyl peroxide, peracetic acid, ammonium cerium(IV) nitrate, hydroxymethanesulfinic acid, and mixtures thereof.

14. The method of claim 12, further comprising the step of applying heat to the hair.

15. The method of claim 12, wherein the composition further comprises from about 0.1% to about 20% of at least one additional compound selected from the group consisting of an ethylenic monomer, a crosslinker, and mixtures thereof, wherein the additional compound has a molecular weight of less than 500 g/mole.

16. The method of claim 15, wherein the composition comprises a crosslinker.

17. The method of claim 16, wherein the crosslinker is selected from the group consisting of 1,4-bisacryloylpiperazine, methylenebisacrylamide, ethylenebisacrylamide, divinylbenzene, poly-ethyleneglycol di(meth)acrylate, ethylene glycol di(meth)acrylate, 1,3-butanediol di(meth)acrylate, 1,4-butanediol di(meth)acrylate, neopentyl glycol di(meth)acrylate, Bis[2-(methacryloyloxy)ethyl]phosphate, N,N'-bis(acryloyl)cystamine, N,N-Diallylacryalmide, triallyl cyanurate, 3-(Acryloyloxy)-2-hydroxypropyl methacrylate and mixtures thereof.

18. A method for preventing color loss from dyed hair comprising the steps of:

a) simultaneously applying to the hair a composition comprising:

i. from about 0.1% to about 20% of an ethylenic monomer selected from the group consisting of sulfopropylacrylate compound, alkylacetamidoacrylate and mixtures thereof, ii. a dermatologically acceptable carrier; and iii. a hair dye.

19. The method of claim 18, wherein the composition further comprises an initiator selected from the group consisting of peroxidisulfates, peroxides, peracids, phosphates, manganates, borates, bis-alkyamidines, sulfites, peroxyesters, bis-cyanocarboxylic acids, alpha-amino acetic acids, sodium peroxydisulfate, 2,2'-azobis(2-methylpropionamidine)dihydrochloride, 2,2'-azobisisobutyronitrile, benzoyl peroxide, peracetic acid, ammonium cerium(IV) nitrate, hydroxymethanesulfinic acid, and mixtures thereof.

20. The method of claim 19, wherein the composition further comprises a crosslinker.

21. The method of claim 20, wherein the crosslinker is selected from the group consisting of 1,4-bisacryloylpiperazine, methylenebisacrylamide, ethylenebisacrylamide, divinylbenzene, poly-ethyleneglycol di(meth)acrylate, ethylene glycol di(meth)acrylate, 1,3-butanediol di(meth)acrylate, 1,4-butanediol di(meth)acrylate, neopentyl glycol di(meth)acrylate, Bis[2-(methacryloyloxy)ethyl]phosphate, N,N'-bis(acryloyl)cystamine, N,N-Diallylacryalmide, triallyl cyanurate, 3-(Acryloyloxy)-2-hydroxypropyl methacrylate and mixtures thereof.

22. A hair care composition comprising:

i. from about 0.1% to about 20% of at least one ethylenic monomer selected from the group consisting of sulfopropylacrylate, alkylacetamidoacrylate and mixtures thereof, and ii. a dermatologically acceptable carrier; and iii. from about 0.1% to about 20% of a crosslinker selected from the group consisting of 1,4-bisacryloylpiperazine, methylenebisacrylamide, ethylenebisacrylamide, divinylbenzene, poly-ethyleneglycol di(meth)acrylate, ethylene glycol di(meth)acrylate, 1,3-butanediol di(meth)acrylate, 1,4-butanediol di(meth)acrylate, neopentyl glycol di(meth)acrylate, Bis[2-(methacryloyloxy)ethyl]phosphate, N,N'-bis(acryloyl)cystamine, N,N-Diallylacryalmide, triallyl cyanurate, 3-(Acryloyloxy)-2-hydroxypropyl methacrylate and mixtures thereof.

\* \* \* \* \*